United States Patent
Yamamoto et al.

(10) Patent No.: US 6,852,885 B2
(45) Date of Patent: Feb. 8, 2005

(54) PRODUCTION METHOD OF HIGH PURITY ORGANIC COMPOUND

(75) Inventors: Hiromasa Yamamoto, Tokuyama (JP); Masao Yamaguchi, Tokuyama (JP); Hideki Kikuchi, Tokuyama (JP)

(73) Assignee: Tokuyama Corporation, Tokuyama (JP)

( * ) Notice: Subject to any disclaimer, the term of this patent is extended or adjusted under 35 U.S.C. 154(b) by 0 days.

(21) Appl. No.: 10/296,319

(22) PCT Filed: Jan. 26, 2001

(86) PCT No.: PCT/JP01/00542

§ 371 (c)(1),
(2), (4) Date: Nov. 22, 2002

(87) PCT Pub. No.: WO01/90033

PCT Pub. Date: Nov. 29, 2001

(65) Prior Publication Data

US 2003/0135068 A1 Jul. 17, 2003

(30) Foreign Application Priority Data

May 22, 2000 (JP) ........................................ 2000-149636

(51) Int. Cl.[7] ...................... C07D 275/02; C07D 67/52; C07D 67/54
(52) U.S. Cl. .......................... 564/32; 560/129; 560/116; 560/117; 548/100; 546/184; 544/2
(58) Field of Search ............................ 564/32; 560/129, 560/116, 117; 548/100; 546/184; 544/2

(56) References Cited

FOREIGN PATENT DOCUMENTS

| JP | 5-265212 A | 10/1993 |
| JP | 11-228459 A | 8/1999 |
| JP | 2000-38362 A | 2/2000 |
| JP | 2000038362 | * 8/2000 |

* cited by examiner

*Primary Examiner*—Rita Desai
(74) *Attorney, Agent, or Firm*—Birch, Stewart, Kolasch & Birch, LLP

(57) ABSTRACT

There is provided a method for obtaining a target organic compound such as an alkyladamantyl ester efficiently by purifying a crude organic compound which contains, as impurities, sublimable materials which start to sublime at temperatures lower than a boiling point of the target organic compound by use of such a simple method as distillation during its production process, without being adversely affected by adherence of the sublimable materials.

The distillation is carried out in the presence of a compound having a boiling point which is lower than a boiling point of the target organic compound, e.g., a carbonyl-group-containing compound. For example, 2-methyl-2-adamantyl methacrylate (boiling point: 92° C./0.3 mmHg) containing sublimable impurities such as adamantane (sublimation starting temperature: room temperature or lower) is distilled in the presence of 1,3-dimethyl-2-imidazolidinone (boiling point: 225° C.).

10 Claims, No Drawings

PRODUCTION METHOD OF HIGH PURITY ORGANIC COMPOUND

This application is the national phase under 35 U.S.C. § 371 of PCT International Application No. PCT/JP01/00542 which has an International filing date of Jan. 26, 2001, which designated the United States of America.

TECHNICAL FIELD

The present invention relates to a method for producing a high purity organic compound. More specifically, it relates to a method for producing a high purity organic compound by distilling and purifying a crude organic compound containing sublimable materials as impurities efficiently.

BACKGROUND ART

Heretofore, when a high boiling compound containing sublimable materials as impurities is distilled and purified, there exist a possibility that the sublimable materials block a pipe by subliming and a problem that solid sublimable materials adhered to the pipe dissolves in a high boiling compound to be distilled out, thereby inhibiting an increase in purity of the high boiling compound. Thus, it has been difficult to distill and purify a high boiling compound containing sublimable materials as impurities.

Meanwhile, demand for products of higher purity has been increasing every year. In particular, a reduction in metal components of a product used in a semiconductor production process is strongly demanded. As a purification method which can remove such metal components efficiently, purification by distillation is suitable.

In recent years, it has been reported that alkyladamantyl (meth)acrylate polymers have high dry etching resistance in a semiconductor production process (refer to JP-A 5-265212), and a possibility of their use as a resist material for a semiconductor has been receiving attention. In the case of these alkyladamantyl(meth)acrylates as well, those having reduced metal components and high purity are desired for use as a resist material for a semiconductor.

It is known that the alkyladamantyl(meth)acrylate can be generally produced by obtaining adamantanone first and then alkyladamantanol from adamantane as a raw material and then reacting the alkyladamantanol with (meth)acrylic acid, (meth)acrylate, (meth)acrylic anhydride or a (meth) acrylic acid halide. However, since the alkyladamantyl (meth)acrylate which is a target compound is a high boiling compound and adamantane, adamantanone and alkyladamantanol remaining as an unreacted raw material and reaction byproducts are sublimable materials having a sublimation starting temperature (sublimation point) lower than a boiling point of the target compound, it has been difficult to purify the target compound efficiently by distillation.

It is an object of the present invention to provide a method for producing a target compound of high purity by applying an efficient purification method to a crude organic compound containing sublimable materials as impurities for which an efficient distillation/purification method has not been known.

The present inventor has made intensive studies to solve the above problem. As a result, he has found that a target organic compound can be efficiently purified by distilling a crude organic compound in the presence of a compound having a boiling point lower than that of the target organic compound. The present invention has been completed by the finding.

DISCLOSURE OF THE INVENTION

To be more specific, the present invention is a method for producing a high purity organic compound by distilling a crude organic compound containing, as impurities, sublimable materials which sublime at temperatures lower than a boiling point of the target organic compound. It comprises the steps of distilling out a compound having a boiling point lower than that of the organic compound by carrying out the distillation in the presence of the compound having a boiling point lower than that of the organic compound so as to cause the compound to rinse out sublimable materials sublimed and adhered to the inside of a distillation device or prevent sublimable materials from adhering to the inside of the distillation device and then distilling out and recovering the organic compound.

In the method of the present invention, a crude organic compound (hereinafter also referred to as "compound to be purified") containing sublimable materials (hereinafter also referred to as "low-temperature sublimable materials") which sublime at temperatures lower than a boiling point of a target organic compound is distilled. The compound to be purified is not particularly limited as long as it is a crude organic compound containing low-temperature sublimable materials. Illustrative examples of the compound to be purified include (i) a reaction solution containing an unreacted raw material which is obtained by synthesizing a target organic compound through a chemical reaction using a sublimable material which sublimes at temperatures lower than a boiling point of the organic compound as a raw material, (ii) a crude product obtained from the reaction solution and containing the raw material as an impurity, (iii) a reaction solution containing sublimable materials which are produced as byproducts when the organic compound is synthesized through the chemical reaction and sublime at temperatures lower than the boiling point of the organic compound and (iv) a crude product obtained from the reaction solution and containing the byproducts as impurities.

An example of an organic compound which inevitably contains sublimable synthesis raw material and reaction byproducts in a synthesis reaction of the organic compound as described above is an alkyladamantyl ester. In a synthesis reaction of the alkyladamantyl ester, a synthesis raw material and byproducts in the synthesis reaction such as adamantane, adamantanone and alkyladamantanol which are sublimable materials are inevitably mixed into the product. The crude organic compound obtained in such a synthesis reaction is suitable as an object to be distilled in the present invention.

The above alkyladamantyl ester is preferably a high boiling compound which has a boiling point at normal pressure of not lower than 100° C. or a boiling point under a reduced pressure of 1 mmHg of not lower than 40° C. Further, the method of the present invention is particularly suitable for a case where a difference between a boiling point of such an organic compound and sublimation starting temperatures of low-temperature sublimable materials is at least 10° C., particularly 20 to 100° C.

For example, an alkyladamantyl ester such as alkyladamantyl(meth)acrylate is produced by obtaining adamantanone first and then alkyladamantanol from adamantane as a raw material and then reacting the alkyladamantanol with a (meth)acrylic acid halide. In this case, obtained reaction solutions or crude products obtained from the reaction solutions generally contain, as impurities, adamantane, adamantanone and alkyladamantanol which are an unreacted raw material and reaction byproducts. Although depending on a degree of vacuum at the time of distillation, these impurities are generally low-temperature sublimable materials whose sublimation starting temperatures are lower than a boiling point of an alkyladamantyl ester which is a target compound by 100 to 10° C. As a method of purifying the target compound from such reaction solutions by distillation, the method of the present invention can be particularly suitably used.

An alkyladamantyl ester produced by the above method is represented by the following formula (1):

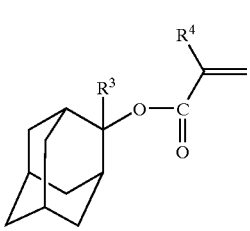

(1)

(wherein $R^3$ is a hydrogen atom or an alkyl group having 1 to 6 carbon atoms, and $R^4$ is a hydrogen atom or a methyl group).

In the above formula (1), $R^3$ is a hydrogen atom or an alkyl group having 1 to 6 carbon atoms, and $R^4$ is a hydrogen atom or a methyl group. Specific examples of the alkyl group having 1 to 6 carbon atoms and represented by $R^3$ include linear alkyl groups such as a methyl group, an ethyl group, a propyl group, a butyl group and a hexyl group; and branched alkyl groups such as an isopropyl group, a tertiary butyl group and a neopentyl group. Particularly, among alkyladamantyl esters represented by the above formula (1), those represented by the formula (1) wherein $R^3$ is a methyl group, an ethyl group or a butyl group and $R^4$ is hydrogen or a methyl group are suitable because they are useful as raw materials for resists for semiconductors and particularly because a high degree of purification is important.

In the present invention, the compound to be purified may also contain a material (hereinafter referred to as "third material") other than the target organic compound and the low-temperature sublimable materials, such as a material without sublimability or a material with sublimability which has a sublimation starting temperature higher than the boiling point of the target organic compound. Generally, a compound which can be the third material is a raw material, byproduct or solvent used at the time of synthesis of the target organic compound.

Further, although composition of the compound to be purified is not particularly limited, the composition is suitably such that the content of the target organic compound is 50 to 99 wt %, particularly 70 to 99 wt %, based on a total weight of the target organic compound and the low-temperature sublimable materials, from the viewpoint of distillation efficiency or the like. Further, when the third material is contained, the content of the third material is suitably not higher than 50 parts by weight, particularly not higher than 30 parts by weight, when the above total weight is 100 parts by weight.

In the present invention, distillation of the compound to be purified is carried out in the presence of a compound (hereinafter also referred to as "distillation assistant") having a boiling point lower than that of the target organic compound so as to purify the target organic compound.

The low-temperature sublimable materials sublime in an early stage of the distillation and solidify and adhere to the inside of distillation devices. The distillation assistant is distilled out concurrently with, right before or right after sublimation of the low-temperature sublimable materials according to its boiling point and exhibits an effect of washing out the low-temperature sublimable materials adhered to the inside of the distillation devices or inhibiting adherence of the low-temperature sublimable materials to the inside of the distillation devices. Therefore, by recovering a distilled-out target organic compound after the low-temperature sublimable materials are discharged by the distillation assistant, the target organic compound to be produced in the present invention can be recovered at a high purity.

The distillation assistant may be any compound having a boiling point which is lower than that of the target organic compound. The boiling point of the distillation assistant may be higher than and equal to or lower than the sublimation starting temperatures of the low-temperature sublimable materials. When the boiling point of the distillation assistant is higher than or equal to the sublimation starting temperatures of the low-temperature sublimable materials, the distillation assistant is distilled out concurrently with or after sublimation of the low-temperature sublimable materials so as to wash out the low-temperature sublimable materials adhered to the inside of the distillation devices. Even if the boiling point of the distillation assistant is lower than the sublimation starting temperatures of the low-temperature sublimable materials, the distillation assistant is distilled out before the sublimation of the low-temperature sublimable materials so as to prevent the low-temperature sublimable materials from adhering to the inside of the distillation devices. As a result, the target compound can be distilled at a high purity.

The distillation assistant is preferably one capable of dissolving the low-temperature sublimable materials in order to recover a high purity organic solvent at a high yield.

When a distillation assistant which is easily separated from the target organic compound is used, the distillation assistant can be removed easily even if the organic compound is distilled out as distillation proceeds and mixed with the distillation assistant, so that the organic compound can be obtained at a high purity. For example, if a water-soluble distillation assistant is used when the organic compound is water-insoluble, the organic compound can be obtained easily by washing a distillate with water. Further, if a water-insoluble distillation assistant is used when the organic compound is easily soluble in water, an acid solution or an alkali solution, the organic compound can be obtained easily by dissolving a distillate in water, an acid solution or an alkali solution, removing the distillation assistant by a liquid separating operation or the like, performing a neutralization operation as required, and removing water. In addition, when the organic compound is insoluble in water and stable in acid or alkali, an acid or alkali distillation assistant can be used. In this case, the organic compound can be obtained easily by washing a distillate with an alkali or acid solution.

An appropriate distillation assistant is determined according to types of the organic compound and low-temperature sublimable materials contained in the compound to be purified. However, a compound containing a carbonyl group can inhibit adherence of the low-temperature sublimable materials to the inside of the distillation devices efficiently and makes it possible to obtain the target organic compound at a high purity even if the content of the organic compound in the compound to be purified is low.

Specific examples of distillation assistants which can be suitably used in the present invention include ethers such as n-butylphenyl ether and dihexyl ether; polyalkylene glycols such as diethylene glycol, triethylene glycol, tetraethylene glycol and dipropylene glycol; sulfoxides and sulfolanes such as dimethyl sulfoxide and sulfolane; phosphoric amides such as hexamethylphosphoric triamide; non-cyclic or cyclic ketones such as benzyl isopropyl ketone, isopropyl phenyl ketone, heptanophenon and methylcyclohexanone; aldehydes such as decanal and benzaldehyde; esters such as diethylene glycol diacetate and phenyl acetate; non-cyclic amides such as dimethylformamide, dipropylformamide, N-benzylacetamide, acetanilide, 1-formylpiperidine, 1-acetylpiperidine, N-formylmorpholine and N,N-diethylacetamide; cyclic amides such as ε-caprolactam, 2-pyrrolidinone, N-methylpyrrolidinone, 1-methyl-2-pyrrolidinone, 1-methyl-2-piperidone, 2-piperidone, 2-pyrrolidone and N-methyl-4-piperidone; non-cyclic ureas such as tetraethylurea, 1,3-diethylurea and 1,1-diethylurea; cyclic ureas such as 1,3-dimethyl-2-imidazolidinone, 1,3-dimethyl-3,4,5,6-tetrahydro-2(1H)-pyrimidinone, ethyleneurea and tetrahydro-2-pyrimidinone; imides such as phthalimide and succinimide; acid anhydrides such as cyclohexanedicarboxylic anhydride; urethanes such as methyl carbamate; and lactides. These distillation assistants may be used alone or in combination of two or more.

Of these distillation assistants, cyclic ureas or cyclic amides represented by the following formula (2):

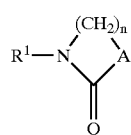

(2)

(wherein $R^1$ is a hydrogen atom or an alkyl group having 1 to 6 carbon atoms, A is —$CH_2$— or >N—$R^2$ (wherein $R^2$ is a hydrogen atom or an alkyl group having 1 to 6 carbon atoms), and n is an integer of 1 to 6) are particularly preferable since they exhibit particularly good solubility to the low-temperature sublimable materials contained in the crude organic compound which is the compound to be purified and the target organic compound can therefore be obtained at a high purity and high yield.

In the above formula (1), $R^1$ and $R^2$ are independently a hydrogen atom or an alkyl group having 1 to 6 carbon atoms. Illustrative examples of the alkyl group include linear alkyl groups such as a methyl group, an ethyl group, a propyl group, a butyl group and a hexyl group; and branched alkyl groups such as an isopropyl group, a tertiary butyl group and a neopentyl group.

Illustrative examples of particularly preferred distillation assistants include cyclic amides such as ε-caprolactam, 2-pyrrolidinone, N-methylpyrrolidinone, 1-methyl-2-pyrrolidinone, 1-methyl-2-piperidone, 2-piperidone, 2-pyrrolidone and N-methyl-4-piperidone; and cyclic ureas such as 1,3-dimethyl-2-imidazolidinone, 1,3-dimethyl-3,4,5,6-tetrahydro-2(1H)-pyrimidinone, ethyleneurea and tetrahydro-2-pyrimidinone.

A manner in which the distillation assistant is caused to be present is not particularly limited as long as it is a manner in which the distillation assistant can wash out low-temperature sublimable materials sublimed and adhered to the inside of the distillation devices or prevent adherence of the low-temperature sublimable materials to the inside of the distillation devices before the target organic compound starts to boil. For example, the distillation assistant may be mixed with the compound to be purified in advance prior to start of distillation or fed directly into a distiller, a distillation column, a distilling tube or a reflux line after start of distillation.

In addition to the above effect of washing out the low-temperature sublimable materials, effects of the distillation assistant include, for example, an effect of facilitating handling of the compound to be purified by decreasing the viscosity of the compound to be purified or changing the compound to be purified into a solution or suspension when the organic compound is solid at room temperature, through addition of the distillation assistant. Further, an effect of achieving such purification by distillation that can be carried out efficiently without deposition of solids during distillation operation (particularly during cooling of a distillate) can also be expected. When these effects are expected in addition to the above wash-out effect, a liquid having a boiling point close to the boiling point of the organic compound is suitably added to the compound to be purified as a second distillation assistant.

The distillation assistant is added in an amount sufficient to wash out all the low-temperature sublimable materials from the distillation devices. The amount of the distillation assistant can be determined in consideration of amounts of the impurities and their solubilities in the distillation assistant and is preferably 0.1 to 100 parts by weight, more preferably 0.2 to 20 parts by weight, based on 1 part by weight of the low-temperature sublimable materials contained in the compound to be purified.

In the production method of the present invention, a manner in which the distillation is carried out in the presence of the distillation assistant is not particularly limited, and simple distillation or fractional distillation is used. In the case of the fractional distillation, as a fractionating column, a thin-film fractionating column such as a vigoureux-type fractional column, a concentric fractional column, a spinning band fractional column and a packed fractional column or a plate fractionating column such as a bubble-cap fractionating column and a porous plate-type fractionating column is suitably used. When vacuum distillation is performed, a thin-film fractionating column which undergoes little pressure loss is particularly suitably used. Further, a known distillation mode such as a Kugel roll or thin-film distillation can be used without any limitations. In addition, distillation conditions including temperature, pressure and a reflux ratio are not particularly limited and may be determined as appropriate according to composition of the compound to be purified, the type and amount of the distillation assistant, purity of the organic compound to be obtained at the end, and the like.

EXAMPLES

Hereinafter, the present invention will be described in more detail with reference to Examples and Comparative Examples. The present invention, however, shall not be limited by these Examples in any way.

Example 1

To 1 part by weight of 2-methyl-2-adamantyl methacrylate with a purity of 72 wt % (boiling point: 92° C./0.3 mmHg) which contained, as sublimable impurities, 2.1 wt % of adamantane (sublimation starting temperature: room temperature or lower), 5.3 wt % of 2-methyleneadamantane (sublimation starting temperature: 30° C.), 4.5 wt % of 2-adamantanone (sublimation starting temperature: 50° C.) and 1.2 wt % of 2-methyl-2-adamantanol (sublimation starting temperature: 60° C.), 0.05 parts by weight of 1,3- dimethyl-2-imidazolidinone (boiling point: 225° C.) was added, and distillation was carried out under a reduced pressure.

The distillation was carried out at a degree of vacuum of 0.3 mmHg by use of a 5-cm vigoureux fractionating column and a whole-condensation-type reflux fractionating device while air was being supplied by means of a glass capillary. Although small amounts of adamantane and the like which were contained as impurities were initially adhered inside the distillation devices, they gradually dissolved and come off after 1,3-dimethyl-2-imidazolidinone had started to be distilled out. The impurities did not cause a blockage. A first distillate was removed, and a main distillate started to be collected at a point where 2-methyl-2-adamantyl methacrylate started to be distilled out. The 2-methyl-2-adamantyl methacrylate did not mix with the 1,3-dimethyl-2-imidazolidinone. From the collected main distillate, 2-methyl-2-adamantyl methacrylate with a purity of 97.7 wt % could be obtained.

Example 2

Distillation was carried out in accordance with Example 1 except that 0.3 parts by weight of N-methylpyrrolidinone (boiling point: 81° C./10 mmHg) was used in place of 1,3-dimethyl-2-imidazolidinone used as a distillation assistant in Example 1. Sublimable impurities which had been initially adhered to the insides of distillation devices gradually dissolved and come off after N-methylpyrrolidinone had started to be distilled out. The impurities did not cause a blockage. In a main distillate, the N-methylpyrrolidinone was mixed with 2-methyl-2-adamantyl methacrylate which was distilled out. However, when the distillate was rinsed with pure water, 2-methyl-2-adamantyl methacrylate with a purity of 95.8 wt % could be obtained.

Example 3

To 1 part by weight of 2-ethyl-2-adamantyl methacrylate with a purity of 82 wt % (boiling point: 96° C./0.2 mmHg) which contained, as sublimable impurities, 6.3 wt % of adamantane, 2.1 wt % of 2-adamantanone and 0.9 wt % of 2-ethyl-2-adamantanol (sublimation starting temperature: 60° C.), 0.1 parts by weight of tetraethylurea (boiling point: 214° C.) and 0.1 parts by weight of 1,3-dimethyl-3,4,5,6-tetrahydro-2(1H)-pyrimidinone (boiling point: 232° C.) were added, and distillation was carried out under a reduced pressure.

The reduced-pressure distillation was carried out at a degree of vacuum of 0.2 mmHg by use of a 5-cm vigoureux fractionating column and a whole-condensation-type reflux fractionating device while air was being supplied by means of a glass capillary.

As a result, the distillation proceeded without any solids precipitated in the distillation devices. After a main distillate was dissolved in hexane and rinsed with pure water, the hexane was removed by distillation. Thereby, 2-ethyl-2-adamantyl methacrylate with a purity of 96.5 wt % could be obtained. When the 2-ethyl-2-adamantyl methacrylate was left to stand at room temperature, it became crystals.

Example 4

To 1 part by weight of 2-butyl-2-adamantyl methacrylate with a purity of 79 wt % (boiling point: 103° C./0.2 mmHg) which contained, as sublimable impurities, 5.1 wt % of adamantane, 1.1 wt % of 2-adamantanone and 0.4 wt % of 2-butyl-2-adamantanol (sublimation starting temperature: 70° C.), 0.1 parts by weight of 1,3-dimethyl-3,4,5,6-tetrahydro-2(1H)-pyrimidinone (boiling point: 232° C.) was added, and distillation was carried out under a reduced pressure in the same manner as in Example 3.

As a result, the distillation proceeded without any solids precipitated in distillation devices. After a main distillate was dissolved in hexane and rinsed with pure water, the hexane was removed by distillation. Thereby, 2-butyl-2-adamantyl methacrylate with a purity of 97.5 wt % could be obtained.

Example 5

To 1 part by weight of 2-methyl-2-adamantyl methacrylate with a purity of 78 wt % (boiling point: 92° C./0.3 mmHg) which contained, as sublimable impurities, 0.05 wt % of adamantane (sublimation starting temperature: room temperature or lower), 2.5 wt % of 2-adamantanone (sublimation starting temperature: 50° C.) and 3.8 wt % of 2-methyl-2-adamantanol (sublimation starting temperature: 60° C.), 0.1 parts by weight of diethylene glycol (boiling point: 245° C.) was added, and distillation was carried out under a reduced pressure.

The reduced-pressure distillation was carried out at a degree of vacuum of 0.3 mmHg by use of a 5-cm vigoureux fractionating column and a whole-condensation-type reflux fractionating device while air was being supplied by means of a glass capillary. Although 2-adamantanone and 2-methyl-2-adamantanol contained as impurities were initially adhered to internal walls of the distillation devices by subliming, they gradually dissolved and come off after diethylene glycol had started to be distilled out. The impurities did not cause a blockage. A first distillate was removed, and then a main distillate started to be collected at a point where 2-methyl-2-adamantyl methacrylate started to be distilled out. The diethylene glycol did not mix with the 2-methyl-2-adamantyl methacrylate and formed a separate layer under the 2-methyl-2-adamantyl methacrylate. By separating the underlying layer from the solution, 2-methyl-2-adamantyl methacrylate with a purity of 97.6 wt % could be obtained.

Example 6

Distillation was carried out in accordance with Example 5 except that N-methylpyrrolidinone (boiling point: 81° C./10 mmHg) was used in place of diethylene glycol used as a distillation assistant in Example 5. Sublimable impurities which had been initially adhered to the insides of distillation devices gradually dissolved and come off after N-methylpyrrolidinone had started to be distilled out. The impurities did not cause a blockage.

In a main distillate, the N-methylpyrrolidinone was mixed with 2-methyl-2-adamantyl methacrylate which was distilled out. However, when the distillate was rinsed with pure water, 2-methyl-2-adamantyl methacrylate with a purity of 97.0 wt % could be obtained.

Example 7

To 1 part by weight of 2-ethyl-2-adamantyl methacrylate with a purity of 86 wt % (boiling point: 96° C./0.2 mmHg) which contained, as sublimable impurities, 0.2 wt % of adamantane, 2.0 wt % of 2-adamantanone and 0.8 wt % of 2-ethyl-2-adamantanol (sublimation starting temperature: 60° C.), 0.1 parts by weight of diethylene glycol (boiling point: 245° C.) and 0.1 parts by weight of tetraethylene glycol (boiling point: 314° C.) were added, and distillation was carried out under a reduced pressure.

The reduced-pressure distillation was carried out at a degree of vacuum of 0.2 mmHg by use of a 5-cm vigoureux fractionating column and a whole-condensation-type reflux fractionating device while air was being supplied by means of a glass capillary.

As a result, the distillation proceeded without any solids precipitated in the distillation devices. After a main distillate was dissolved in hexane and rinsed with pure water, the hexane was removed by distillation. Thereby, 2-ethyl-2-adamantyl methacrylate with a purity of 96.3 wt % could be obtained. When the 2-ethyl-2-adamantyl methacrylate was left to stand at room temperature, it became crystals.

Example 8

To 1 part by weight of 2-butyl-2-adamantyl methacrylate with a purity of 85 wt % (boiling point: 103° C./0.2 mmHg) which contained, as sublimable impurities, 0.1 wt % of adamantane, 1.0 wt % of 2-adamantanone and 0.5 wt % of 2-butyl-2-adamantanol (sublimation starting temperature: 70° C.), 0.1 parts by weight of tetraethylene glycol (boiling point: 314° C.) was added, and distillation was carried out under a reduced pressure in the same manner as in Example 7.

As a result, the distillation proceeded without any solids precipitated in distillation devices. After a main distillate was dissolved in hexane and rinsed with pure water, the hexane was removed by distillation. Thereby, 2-butyl-2-adamantyl methacrylate with a purity of 97.5 wt % could be obtained.

Although some portions of adamantane and the like which were contained as impurities were initially adhered to walls of the distillation devices by sublimation, they gradually dissolved and come off after 1,3-dimethyl-2-imidazolidinone had started to be distilled out. The impurities did not cause a blockage. A first distillate was removed, and a main distillate started to be collected at a point where purity of 2-methyl-2-adamantyl methacrylate exceeded 80%. From the collected main distillate, 2-methyl-2-adamantyl methacrylate with a purity of 97.7 wt % could be obtained.

Examples 10 to 19

Distillations were conducted in accordance with Example 9 except that various distillation assistants shown in Table 1 were used in place of 1,3-dimethyl-2-imidazolidinone used as a distillation assistant in Example 9. When a main distillate contained a distillation assistant, the main distillate was dissolved in hexane and then rinsed with pure water and then the hexane was removed by distillation so as to obtain a target product.

The results are also shown in Table 1. Even if a large amount of low-temperature sublimable materials were contained, adhesion of the low-temperature sublimable materials could be inhibited effectively when a compound containing a carbonyl group was used as a distillation assistant.

| Ex.No. | Distillation Assistant Type | Amount Added (Parts by Weight) | Purity of Target Product in Main Distillate (wt %) |
|---|---|---|---|
| 10 | 1,3-dimethyl-3,4,5,6-tetrahydro-2(1H)-pyrimidinone (boiling point: 232° C.) | 0.1 | 98.1 |
| 11 | 1-methyl-2-piperidone (boiling point: 225° C.) | 0.1 | 98.2 |
| 12 | 2-piperidone (boiling point: 256° C.) | 0.1 | 98.0 |
| 13 | 1,3-dimethyl-2-imidazolidinone (boiling point: 225° C.) | 0.05 | 97.4 |
|  | 1-acetylpiperidine (boiling point: 224° C.) | 0.05 |  |
| 14 | 1-formylpiperidine (boiling point: 220° C.) | 0.1 | 95.5 |
| 15 | isopropyl phenyl ketone (boiling point: 226° C.) | 0.1 | 95.3 |
| 16 | N,N-diethylacetacetamide (boiling point: 110° C./10 mmHg) | 0.1 | 94.2 |
| 17 | diethylene glycol diacetate (boiling point: 245° C.) | 0.1 | 95.7 |
| 18 | diethylene glycol (boiling point: 245° C.) | 0.1 | 91.3 |
| 19 | dihexyl ether (boiling point: 226° C.) | 0.1 | 89.7 |

Ex.: Example

Example 9

To 1 part by weight of 2-methyl-2-adamantyl methacrylate with a purity of 65 wt % (boiling point: 92° C./0.3 mmHg) which contained, as sublimable impurities, 0.1 wt % of adamantane (sublimation starting temperature: room temperature or lower), 12.4 wt % of 2-methyleneadamantane (sublimation starting temperature: 40° C.), 6.3 wt % of 2-adamantanone (sublimation starting temperature: 50° C.) and 2.7 wt % of 2-methyl-2-adamantanol (sublimation starting temperature: 60° C.), 0.1 parts by weight of 1,3-dimethyl-2-imidazolidinone (boiling point: 225° C.) was added, and distillation was carried out under a reduced pressure.

The distillation was carried out at a degree of vacuum of 0.3 mmHg by use of a 5-cm vigoureux fractionating column and a whole-condensation-type reflux fractionating device while air was being supplied by means of a glass capillary.

Comparative Example 1

When reduced-pressure distillation was carried out without adding anything to 2-methyl-2-adamantyl methacrylate with a purity of 79 wt % which was used in Example 1, cooling pipes of distillation devices were blocked by sublimable solids, thereby inhibiting the distillation.

Comparative Example 2

When reduced-pressure distillation was carried out without adding anything to 2-methyl-2-adamantyl methacrylate with a purity of 65 wt % which was used in Example 9, cooling pipes of distillation devices were blocked by sublimable solids, thereby inhibiting the distillation.

As described above, according to the production method of the present invention, sublimable materials which sublime and adhere to pipes and the like at an initial stage of distillation can be dissolved or come off upon sublimation of the sublimable materials or by a distillation assistant which is distilled out after the sublimable materials, thereby preventing the sublimable materials from blocking the pipes and/or dissolving in an organic compound. Further, even if a distillation assistant is mixed into an organic compound, it can be removed easily, thereby making it possible to distill and purify an organic compound efficiently.

According to the present invention, a high boiling compound which has heretofore been difficult to distill and purify, i.e., a high boiling compound containing sublimable materials as impurities, can be distilled and purified easily. In addition, by use of the production method of the present invention, a high purity alkyladamantyl ester which is considered promising as a resist material for a semiconductor can be obtained easily.

What is claimed is:

1. A method for producing a high purity alkyladamantyl ester at a purity of 89.7% or higher represented by the following formula (1):

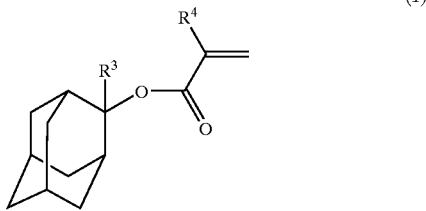

(1)

wherein $R^3$ is a hydrogen atom or an alkyl group having 1 to 6 carbon atoms and $R^4$ is a hydrogen atom or a methyl group which contains as impurities, sublimable materials which sublime at temperatures lower than a boiling point of the alkyladamantyl ester, comprising the steps of distilling out a compound having a boiling point lower than that of the alkyladamantyl ester by carrying out the distillation in the presence of the compound having a boiling point lower than that of the alkyladamantyl ester so as to cause the compound to rinse out sublimable materials sublimed and adhered to the inside of a distillation device or prevent sublimable materials from adhering to the inside of the distillation device and then distilling out and recovering the alkyladamantyl ester.

2. The method of claim 1, wherein the sublimable materials are compounds having sublimation starting temperatures lower than the boiling point of the target organic compound by 100 to 10° C.

3. The method of claim 1, wherein the sublimable materials are adamantane, adamantanone and alkyladamantanol.

4. The method of claim 1, wherein the compound having a boiling point lower than that of alkyladamantyl ester is an ether, polyalkylene glycol, sulfoxide, sulfolane, phosphoric acid amide, non-cyclic or cyclic ketone, aldehyde, ester, non-cyclic or cyclic amide, non-cyclic or cyclic urea, imide, acid anhydride, urethane or lactide.

5. The method of claim 1, wherein the compound having a boiling point lower than that of the alkyladamantyl ester is water-soluble, acid solution-soluble or basic solution-soluble.

6. The method of claim 1, wherein the compound having a boiling point lower than that of an alkyladamantyl ester is a cyclic urea or cyclic amide represented by the following formula (2):

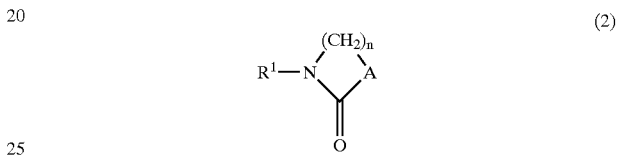

(2)

wherein $R^1$ is a hydrogen atom or an alkyl group having 1 to 6 carbon atoms, A is —$CH_2$— or >N—$R^2$ wherein $R^2$ is a hydrogen atom or an alkyl group having 1 to 6 carbon atoms, and n is an integer of 1 to 6.

7. The method of claim 1, wherein the compound having a boiling point lower than that of the alkyladamantyl ester is present in an amount of 0.1 to 100 parts by weight per part by weight of the sublimable material.

8. The method of claim 1, wherein the high purity alkyladamantyl ester is obtained at a purity of 96.5% or higher.

9. The method of claim 2, wherein the high purity alkyladamantyl ester is obtained at a purity of 96.5% or higher.

10. The method of claim 5, wherein the high purity alkyladamantyl ester is obtained at a purity of 96.5% or higher.

* * * * *